United States Patent [19]
Dalton et al.

[11] 4,156,016
[45] May 22, 1979

[54] INDOLE COMPOUNDS AND PROCESS FOR THEIR PREPARATION

[75] Inventors: Colin Dalton, Upper Montclair; Kenneth E. Fahrehnoltz, Bloomfield; Mary Z. Silverzweig, Mendham, all of N.J.

[73] Assignee: Hoffmann-La Roche Inc., Nutley, N.J.

[21] Appl. No.: 774,072

[22] Filed: Mar. 3, 1977

[51] Int. Cl.$^2$ ............... C07D 209/18; C07D 209/12; C07D 209/14; C07D 209/08

[52] U.S. Cl. ............... 260/326.13 C; 260/326.16; 260/193; 424/274

[58] Field of Search ............... 260/326.13 C, 326.16; 424/274

*Primary Examiner*—Donald G. Daus
*Assistant Examiner*—D. B. Springer
*Attorney, Agent, or Firm*—Jon S. Saxe; Bernard S. Leon; George W. Johnston

[57] ABSTRACT

Indole compounds having utility as blood platelet aggregation inhibitors and as intermediates in the production of 1,4-benzodiazepines are disclosed.

6 Claims, No Drawings

INDOLE COMPOUNDS AND PROCESS FOR THEIR PREPARATION

BACKGROUND OF THE INVENTION

Indole-2-carboxamides and indole-2-carbonitriles are well known types of compounds and in recent years have been extensively reported as intermediates in the synthesis of 1,4-benzodiazepines. See, for example, Yamamoto et al., *Chem. Ber.*, 101, pages 4245–4247 (1968); Inaba et al., *Chem. Pharm. Bull.*, 19, pages 263–272 (1971); Inaba et al., Ibid, pages 722–729; Inaba et al., *Chem. Pharm. Bull.*, 20, pages 1628–1636 (1972); Inaba et al., *Chem. Pharm. Bull.*, 23, pages 3279–3282 (1975); Asami et al., *Arzneim.-Forsch.*, 25, pages 534–539 (1975); Inaba et al., *Chem. Pharm. Bull.*, 24, pages 1076–1082 (1976). These amides and nitriles are usually made from the corresponding esters and/or acids by standard procedures. However, problems are encountered when employing these standard procedures, in particular, lengthy and involved reaction steps resulting in intermediates which require separation and purification. Efficient use of these standard procedures is also impaired when the starting materials or intermediates contain functional groups which are reactive under the standard reaction conditions.

An object of this invention is to provide a simplified procedure for the preparation of indole-2-carboxamides and indole-2-carbonitriles.

Certain of the indoles disclosed herein have been found to possess blood-platelet aggregation inhibitory properties.

Blood platelets, sometimes referred to as thrombocytes, are anucleate cells which exist in large numbers in normal mammalian blood and form a vital part of the complex hemostatic mechanism. When blood vessels are injured and bleeding occurs, blood platelets adhere to subendothelial tissue in the damaged vessel wall and then clump or aggregate to form a platelet plug which arrests the bleeding. This platelet plug is then consolidated by the formation of a network of fibrin which results from activation of the blood clotting system. The pathological extension of the normal hemostatic platelet plug is called a thrombus. This may occur in vessels where the inner wall is injured and bleeding does not occur as, e.g., in atherosclerosis. During thrombus formation, emboli (consisting of platelet aggregates or particles of the more developed thrombus) may go downstream in the blood, lodge in small vessels to completely occlude them and block the flow of blood to a major organ. Thrombosis appears to play an important etiological role or complicating factor in a large number of disease states. While controversy continues as to the casual role of blood-platelet aggregation in atherosclerosis, it is accepted that such platelet aggregation accelerates the narrowing and eventual closure of the vascular lumen begun by the atherosclerotic plaque.

A factor which may be involved in these pathological (thrombocytopathic) phenomena is abnormal blood-platelet adhesiveness. Regardless of the mechanism, it is generally conceded that thrombosis plays a critical role in stroke, pulmonary embolism and myocardial infarction. It is generally believed that if this tendency toward undesired platelet aggregation or adhesiveness could be reduced, the incidence of thrombotic episodes would be reduced.

Certain prostaglandins, particularly those of the "E" series, such as (11,13E,15S)-11,15-dihydroxy-9-oxoprost-13-en-1-oic acid (PGE$_1$), (8$\beta$,11$\alpha$,13E,15S)-11,15-dihydroxy-9-oxoprost-13-en-1-oic acid (8-iso-PGE$_1$) and (11$\alpha$,13E,15S)-11,15-dihydroxy-20-methyl-9-oxoprost-13-en-1-oic acid ($\omega$-homo PGE$_1$) have been demonstrated to inhibit platelet aggregation, Kloeze, *Biochim. Biophys. Acta*, 187, pages 285–292 (1969); and Serhar et al., *Circulation*, 38, Supp. 6, pages VI-23 (1968). However, while the above disclosed prostaglandins are known to possess platelet anti-aggregating properties, their use for preventing thrombosis has been seriously limited because their anti-aggregating properties are rapidly destroyed in the circulation during passage through the lungs by an enzyme (PG dehydrogenase) which converts the 15-OH function to a ketone. The administration of these prostaglandins is also associated with several undesirable side effects. Additionally, the prostaglandins of the "E" series readily undergo autooxidation to other forms of prostaglandins that lack platelet anti-aggregation properties: Shaw et al., *Meth. Biochem. Anal.*, 17, pages 325–371 (1969). Thus, in view of this presentation, it becomes immediately apparent that a critical need exists for a method for inhibiting aggregation of platelets that is essentially free from the tribulations associated with the prior art. Likewise, it will be further apparent that if a new and useful method for protecting platelets is made available to the art, especially wherein the platelet anti-aggregation agent possesses stability, said method would have a positive medical value and it would also present a substantial contribution to the art.

Smith et al. in the *Brit. J. Pharmacology*, 40, pages 545P–546P (1970) demonstrated that human blood platelets can form and release prostaglandins PGE$_2$ and PGF$_{2\alpha}$ when the washed platelets are treated with thrombin. Silver et al. in *Prostaglandins*, 1, pages 429–436 (1972) showed that these prostaglandins were formed during blood clotting. They are also formed during the aggregation of platelets in platelet-rich plasma in response to collagen, epinephrine, adenosine diphosphate (ADP); Smith et al., *J. Clin. Invest.*, 52, pages 965–969 (1973). The precursor of these prostaglandins is arachidonic acid ((all Z)-5,8,11,14-eicosatetraenoic acid). It has been shown that arachidonic acid induces both platelet aggregation and prostaglandin synthesis. During the bioconversion of arachidonic acid to PGE$_2$, PGF$_{2\alpha}$, and other polar products which occur in platelets, thromboxanes transiently accumulate. Thromboxanes induce platelet aggregation. Thromboxanes can also induce the release of aggregatory substances from stores within the platelet. The biological effects of thromboxanes are potentiated (up to ~700%) in the presence of submicrogram concentrations of PGE$_2$; Silver et al. *Prostaglandins*, 4, pages 863–875, (1973). That thromboxanes may be the causative factor in arterial thrombosis is based on the fact that aspirin, which has anti-thrombotic properties in laboratory animal models of arterial thrombosis, inhibits the biosynthesis of thromboxanes.

A further object of this invention is to provide a method of inhibiting or preventing blood-platelet aggregation by the use of certain indoles.

SUMMARY OF THE INVENTION

The instant invention provides a process for the preparation of compounds of the formula

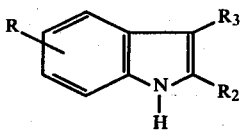

wherein R is hydrogen, halogen, C(CX$_3$)$_2$OH, nitro, carboxy or lower alkoxycarbonyl; R$_2$ is cyano or carboxamido, or lower alkoxycarbonyl; and R$_3$ is hydrogen, aryl or lower alkyl
which comprises reacting a compound of the formula

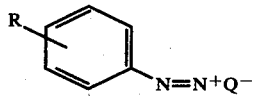

wherein R is as above and Q is the anion of an acid used under diazotization conditions
with a compound of the formula

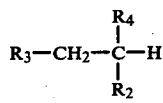

wherein R$_2$ and R$_3$ are as above, and R$_4$ is lower acyl, carboxy or lower alkoxycarbonyl
to form a compound of the formula

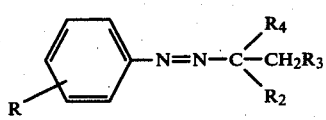

wherein R, R$_2$, R$_3$ and R$_4$ are as above followed by acid treatment of compound IV to obtain compounds of formula I.

The instant invention also relates to a method of inhibiting blood-platelet aggregation by the administration, either orally or parenterally, to a patient disposed toward undesirable platelet aggregation, of certain indole compounds of formula I.

Although there are materials known to have blood platelet anti-aggregation properties, e.g., aspirin, indomethacin, adenosine and sodium salicylate, these materials normally possess the disadvantages of limited effectiveness and long-term toxic effects. Distinct advantages of using the indoles disclosed herein are (1) low acute toxicity and (2) lack of formation of gastric ulcers.

This invention provides an effective means of inhibiting blood-platelet aggregation without the side-effects and disadvantages of platelet-aggregation inhibitors known heretofore.

DETAILED DESCRIPTION OF THE INVENTION

As used throughout this application the terms "halo" and "halogen" connote chlorine, bromine, fluorine or iodine. The term "lower alkyl" refers to straight or branched chain alkyl groups having from 1-8 carbon atoms. Typical lower alkyl groups include methyl, ethyl, isopropyl and the like. The term "lower alkoxy" refers to alkoxy groups, the lower alkyl moiety of which is as defined above. Typical lower alkoxy groups include methoxy, ethoxy, propoxy, isopropoxy and the like. The term "lower alkoxycarbonyl" refers to ester groups where the alkoxy moiety is as defined above. The term "lower acyl" as used herein refers to acyl groups having from 1-6 carbon atoms having either straight or branched chains. Typical lower acyl groups are formyl, acetyl, propionyl, butyryl and the like.

The term "carboxamido" refers to carboxamido groups which may be unsubstituted or substituted at the nitrogen moiety by either one or two lower alkyl groups. Typical carboxamido groups are carboxamide, N,N-dimethylcarboxamide, N-butylcarboxamide and the like. The term "lower alkanol" refers to alkanols having a lower alkyl moiety as defined above. The term "alkali metal" refers to sodium, potassium and lithium. The term "alkaline earth metal" refers to barium, calcium, magnesium and strontium. The term "aryl" as used herein connotes mono-nuclear aryl groups such as phenyl which can be unsubstituted or substituted in one or more positions with a lower alkyl, halogen, amino, lower alkoxy, nitro, or mono- and di-lower alkylamino groups. The term "aryl" also encompasses polynuclear aryl groups such as naphthyl, phenanthryl and the like.

A compound of the formula I is prepared by diazotizing a compound of the formula

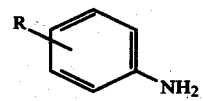

wherein R is as previously defined
to form a compound of the formula

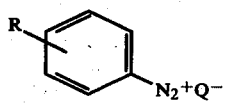

wherein R and Q are as previously defined.

The transformation of compound Ib to compound II is carried out employing standard diazotization techniques. Preferably, the reaction is carried out in an aqueous solution of an acid capable of protonating a diazotizable amine, preferably hydrochloric, sulfuric, trifluoroacetic and acetic acids, at a temperature of about 0° C. in the presence of sodium nitrite or a lower alkyl nitrite.

Compound II is then reacted with a compound of the formula

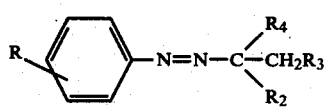

wherein R$_2$, R$_3$ and R$_4$ are as defined above
to form a compound of the formula

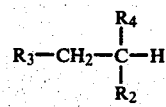

wherein R, R$_2$, R$_3$ and R$_4$ are as defined above.
Compounds having the formula

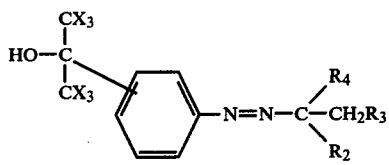

IVa wherein X is chlorine or fluorine; and $R_2$, $R_3$ and $R_4$ are as previously defined are novel and as such form an aspect of this invention.

The preparation of compounds of formula IV or IVa is conducted via a diazonium coupling reaction between compounds of formula II and III. The reaction between compounds II and III is generally carried out in an aqueous lower alkanol solution in the presence of a base. The reaction is carried out at a temperature varying from $-10°$ C. to $25°$ C., preferably from about $-5°$ C. to about $5°$ C.

Although aqueous lower alkanols are generally employed in the reaction between compounds II and III, any solvent in which the diazonium salt is non-reactive may be employed. Typical solvents are benzene, ethyl ether, chloroform, dioxane, tetrahydrofuran (THF) and carbon tetrachloride. Typical bases that may be employed are alkali and alkaline earth metal hydroxides such as sodium hydroxide, potassium hydroxide, barium and calcium hydroxides. Alkali and alkaline earth metal salts of monocarboxylic acids, e.g., sodium acetate, are particularly preferred as bases in this reaction.

Compounds IV or IVa are then treated with an acid to form hydrazones of the formulas

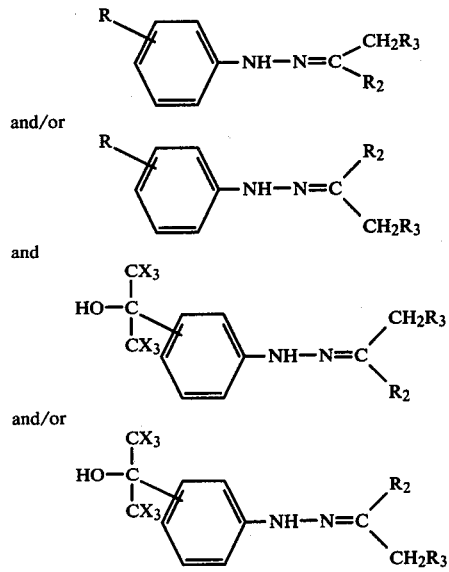

wherein R, $R_2$, $R_3$, $R_4$ and X are as above.

Compounds of formula Va and Va' are novel and as such form another aspect of this invention.

The hydrazone formation is generally carried out at room temperature in the presence of an acid. Typical acids that may be employed are inorganic acids such as hydrochloric, sulfuric, phosphoric and the like. Organic acids, preferably lower alkyl monocarboxylic acids such as acetic acid and the like may also be employed. Acidic compounds such as $ZnCl_2$ may also be used.

The combination of the reaction between compounds II and III to form compounds IV and IVa followed by conversion into compounds V and Va and/or V' and Va' together form an example of the Japp-Klingemann reaction. The products of this reaction are generally obtained as a mixture of syn and anti isomers V and V' and Va and Va'. If desired, the less stable isomer can be converted into the more stable isomer by treatment with acid at a temperature from room temperature to about $50°$ C. (preferably about $35°$ C.).

Upon further heating under acid conditions, compounds V and Va are converted by the Fischer indole synthesis to compounds of the formula I and

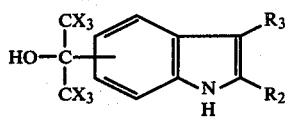

Ia respectively, wherein $R_2$, $R_3$ and X are as previously defined.

Compounds of formula Ia are novel and as such form another aspect of this invention.

Compounds I and Ia are obtained by treating compounds V or Va, respectively, with an inorganic acid, an organic acid or mixtures thereof at temperatures of from about $70°$ C. to about $125°$ C., preferably about $80°$ C.-$100°$ C. The acids employed may be the same as those mentioned hereinabove. Also among the acidic compounds that may be used are $P_2O_5$, polyphosphoric acid, polyphosphate ester, $ZnCl_2$ and $TiCl_4$. This cyclization may be conducted in a solvent which is inert to the particular acid employed.

An alternative procedure for the preparation of compounds I or Ia is the treatment of compounds IV or IVa with an acid system as described hereinabove but at a temperature of about $70°$ C. to about $125°$ C., preferably about $80°$ C. to about $100°$ C. Compounds I and Ia are obtained directly without isolation of either compound V or Va, respectively. HCl in ethanol or polyphosphate ester are particularly preferred for the conversion of compounds IV or IVa directly to compounds I or Ia.

Compounds of formula I, where $R_2$ is a cyano or unsubstituted carboxamido, are intermediates for the preparation of 1,4-benzodiazepines. These compounds are made from the corresponding compounds of formula I where $R_2$ is carboxy or lower alkoxycarbonyl which are themselves made via a Japp-Klingemann reaction followed by a Fischer indole cyclization. The compounds of formula I where $R_2$ is lower alkoxycarbonyl in some cases can be converted into compounds of formula I where $R_2$ is unsubstituted carboxamido by treatment with ammonia. More generally, the compounds of formula I where $R_2$ is lower alkoxycarbonyl are converted into compounds of formula I where $R_2$ is carboxy by basic hydrolysis. Bases that may be used are those alkali and alkaline earth hydroxides mentioned hereinbefore. This is then followed by the formation of compounds of formula I where $R_2$ is halocarbonyl by treatment of the acid with typical reagents such as $PCl_3$, $COCl_2$, $PCl_5$, $POCl_3$ and other standard halogen substituting reagents. The compounds of formula I where $R_2$ is unsubstituted carboxamido are then obtained by treating the compounds of formula I where $R_2$ is halocarbonyl with excess ammonia. Dehydration of the compounds of formula I where $R_2$ is unsubstituted carboxamido then yields the compounds of formula I where $R_2$ is cyano.

The present invention provides a novel synthesis of the desirable compound of formula I where $R_2$ is cyano or carboxamido by the reaction of compound II with a compound of the formula

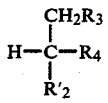   IIIa wherein $R'_2$ is cyano or carboxamido; and $R_3$ and $R_4$ are as defined above
to form a compound of the formula

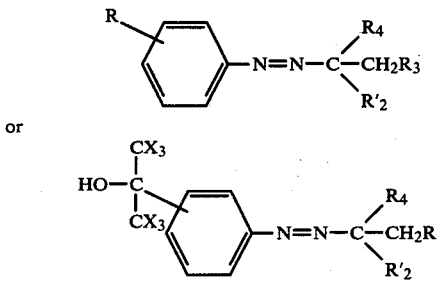

IVb or

IVc wherein R, $R'_2$, $R_3$, $R_4$ and X are as previously defined
followed by acid treatment employing the same conditions utilized in reacting compounds II, III, IV and V. By $R'_2$ being a cyano or carboxamido the need to prepare compound I where $R_2$ is lower alkoxycarbonyl, carboxy or halocarbonyl is obviated by this direct preparation of compound I where $R_2$ is cyano or carboxamido via the Japp-Klingemann reaction and Fischer indole synthesis.

In addition, the present invention provides a novel synthesis of the desirable compound I where $R_2$ is cyano by the treatment of a compound of the formula

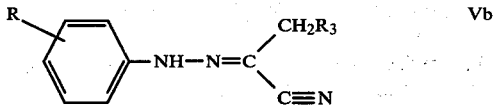   Vb wherein R and $R_3$ are as previously defined
under the same conditions utilized in reacting compound V. When compound I where $R_2$ is cyano is desired, the use of compound Vb as a starting material in this Fischer indole synthesis obviates the need to prepare compound I where $R_2$ is lower alkoxycarbonyl, carboxy, halocarbonyl or carboxamido.

Certain indoles of the formula I have been found to inhibit prostaglandin formation and human blood-platelet aggregation. In addition, these compounds have been found to be non-ulcerogenic and low in toxicity. In particular, among the indoles found to have the foregoing properties are those of the formula

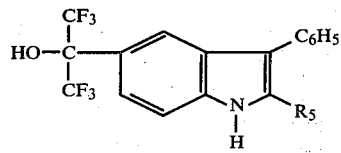

wherein $R_5$ is

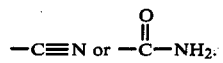

These indoles will be referred to hereinafter as the "nitrile" and the "amide", respectively. Furthermore, in contrast to other known prostaglandin inhibitors, the "nitrile" is devoid of central and peripheral pharmacological activity.

Aspirin and indomethacin are known inhibitors of platelet prostaglandin formation. However, these compounds have a strong ulcerogenic potential and possess central and peripheral pharmacological activity.

The "nitrile" and the "amide" can be added to whole blood as kept in blood banks, whole blood as used in heart-lung machines, and platelet-rich concentrates.

It has been found that the foregoing indoles inhibit platelet aggregation at doses between 1–100 mg/kg of body weight, preferably about 1–30 mg/kg of body weight per day.

The compounds of this invention can be administered to mammals disposed toward undesirable (excessive) blood-platelet aggregation. Individuals can be disposed to hyperthrombotic complications due to surgery, late pregnancy, phlebitis, atherosclerosis, recent myocardial infarction and the like. The compounds of the invention are particularly suited for administration to patients who have just had artificial heart valves inserted and therefore face a serious risk of thromboembolism from platelet thrombi. It is also contemplated that the process of this invention can be employed as long term prophylactic treatment of persons disposed to excessive platelet aggregation. The compounds of this invention can be administered either orally or parenterally. The oral route is preferred for chronic and prophylactic use. Parenteral use is indicated for those excessively prone to acute thromboembolic episodes, and when immediate onset of activity is desired. In each specific instance, the attending diagnostician will determine the exact dosage, amount and frequency talking into account related health factors of the subject.

For oral use, the compounds employed herein can be combined with conventional compatible organic or inorganic pharmaceutical carrier materials known in the art. Such materials include, for example, water, gelatin, gums, lactose, starches, magnesium stearate, talc, vegetable oils, polyalkylene glycols, petroleum jelly and the like. Such pharmaceutical preparations may be in unit dosage form and may additionally contain other therapeutically valuable substances or conventional pharmaceutical adjuvants such as preservatives, stabilizing agents, wetting agents, emulsifying agents, buffers and the like. The pharmaceutical preparations can be in conventional solid dosage forms such as tablets, capsules, dragees and the like, conventional liquid forms such as solutions, suspensions, emulsions and the like and other conventional dosage forms such as dry ampules, suppositories and the like. Such preparations may be submitted to conventional pharmaceutical expedients such as, for example, sterilization and the like.

For parenteral use, the compounds employed herein can be administered in conventional pharmaceutical forms, for example, solutions, suspensions and emulsions. Examples of conventional pharmaceutical carrier materials which may be utilized in such forms include, for example, water for injection, vegetable oils, polyalkylene glycols and the like. Such preparations can be subjected to conventional pharmaceutical expedients such as sterilization and can contain conventional pharmaceutical adjuvants such as preservatives, stabilizing agents, wetting agents, emulsifying agents, salts for the adjustment of osmotic pressure, buffers and the like. The composition can also contain other therapeutically active materials.

The following examples illustrate the invention. In these examples, all the assigned structures have been confirmed by standard spectroscopic techniques. All temperatures are in degrees Centigrade.

EXAMPLE 1

3-Phenyl-5-[2,2,2-trifluoro-1-hydroxy-1-(trifluoromethyl)ethyl]indole-2-carboxylic acid ethyl ester To a solution of 95.0 g. (0.367 mol) of 4-[2,2,2-trifluoro-1-hydroxy-1-(trifluoromethyl)ethyl]benzenamine in 300 ml. of water and 155 ml. of concentrated hydrochloric acid cooled to and kept at 0° was added a solution of 28.5 g. (0.40 mol) of sodium nitrite in 50 ml. of water. The reaction mixture was stirred until it became homogeneous and then added over 45 minutes to a soluton of 81.0 g. (0.367 mol) of α-acetylbenzenepropanoic acid ethyl ester and 155 ml. of 50% potassium hydroxide solution in 800 ml. of 50% aqueous ethanol cooled to and kept at −10°. The cooling bath was removed, the reaction was stirred for 20 minutes and extracted with 1 l. of dichloromethane and then with 500 ml. portions of dichloromethane until the extract was colorless. The combined extracts were passed over a column of 500 g. of silica gel which was then washed with 1:1 ether-dichloromethane. The combined eluates were concentrated to give 190 g. of crude α-acetyl-α-[4-[2,2,2-trifluoro-1-hydroxy-1-(trifluoromethyl)ethyl]phenylazo]benzenepropanoic acid ethyl ester and/or α-[1-[4-[2,2,2-trifluoro-1-hydroxy-1-(trifluoromethyl)ethyl]phenyl]hydrazin-2-ylidene]benzenepropanoic acid ethyl ester as a reddish oil. This was mixed with 250 ml. of acetic acid and 250 ml. of concentrated hydrochloric acid and heated under reflux for 30 minutes. The solution was kept in the refrigerator overnight. The resulting precipitate was collected by filtration and washed with water and with chloroform to give 81.0 g. (51%) of 3-phenyl-5-[2,2,2-trifluoro-1-hydroxy-1-(trifluoromethyl)ethyl]indole-2-carboxylic acid ethyl ester as yellow crystals, m.p. 185°–193°. Recrystallization from ether-dichloromethane gave colorless crystals, m.p. 194°–195.5°.

Anal. Calcd for $C_{20}H_{15}F_6NO_3$: C, 55.69; H, 3.51; F, 26.43; N, 3.25. Found: C, 55.59; H, 3.39; F, 26.17; N, 3.22.

EXAMPLE 2

3-Phenyl-5-[2,2,2-trifluoro-1-hydroxy-1-(trifluoromethyl)ethyl]indole-2-carboxylic acid A solution of 26.65 g. (0.062 mol) of 3-phenyl-5-[2,2,2-trifluoro-1-hydroxy-1-(trifluoromethyl)ethyl]indole-2-carboxylic acid ethyl ester and 6.35 g. of sodium hydroxide in 330 ml. of ethanol was heated under reflux for 75 minutes. Most of the ethanol was evaporated, the residue was diluted with water and washed with ether. The aqueous solution was then acidified with hydrochloric acid and extracted with ether which was dried and evaporated. The residual oil was taken up in benzene and evaporated several times to remove occluded ether. The resulting colorless oil was recrystallized from benzene to give in several crops 24.5 g. (98%) of 3-phenyl-5-[2,2,2-trifluoro-1-hydroxy-1-(trifluoromethyl)ethyl]indole-2-carboxylic acid, m.p. 175°–179°. The analytical sample was obtained by concentration of a moist ether solution to give colorless crystals of the hemihydrate of 3-phenyl-5-[2,2,2-trifluoro-1-hydroxy-1-(trifluoromethyl)ethyl]indole-2-carboxylic acid, m.p. 185.5°–190°.

Anal. Calcd for $C_{18}H_{11}F_6NO_3.0.5H_2O$: C, 52.40; H, 2.93; F, 27.65; N, 3.40. Found: C, 52.29; H, 2.85; F, 27.50; N, 3.36.

EXAMPLE 3

3-Phenyl-5-[2,2,2-trifluoro-1-hydroxy-1-(trifluoromethyl)ethyl]indole-2-carboxamide A mixture of 24.5 g. (0.061 mol) of 3-phenyl-5-[2,2,2-trifluoro-1-hydroxy-1-(trifluoromethyl)ethyl]indole-2-carboxylic acid, 13.0 g. of phosphorus pentachloride and 250 ml. of ether was heated under reflux for one hour. The resulting clear yellow solution containing 3-phenyl-5-[2,2,2-trifluoro-1-hydroxy-1-(trifluoromethyl)ethyl]indole-2-carbonyl chloride was added over 15 minutes to a solution of 100 ml. of ammonia in 350 ml. of ether cooled in a dry ice-acetone bath. The cooling bath was removed and with efficient stirring the slurry was gradually warmed to remove the excess ammonia. The resulting colorless suspension was filtered through a filter-aid and concentrated to an oil which soon crystallized. Recrystallization from ether-benzene gave 22.2 g. (91%) of 3-phenyl-5-[2,2,2-trifluoro-1-hydroxy-1-(trifluoromethyl)ethyl]indole-2-carboxamide, m.p. 228°–230°. The analytical sample was obtained from etherhexane and had m.p. 228.5°–231°.

Anal. Calcd. for $C_{18}H_{12}F_6N_2O_2$: C, 53.74; H, 3.01; F, 28.34; N, 6.96. Found: C, 53.69; H, 3.01; F, 28.05; N, 6.99.

EXAMPLE 4

3-Phenyl-5-[2,2,2-trifluoro-1-hydroxy-1-(trifluoromethyl)ethyl]indole-2-carboxamide Hydrogen chloride was bubbled into a solution of crude α-acetyl-α-[4-[2,2,2-trifluoro-1-hydroxy-1-(trifluoromethyl)ethyl]phenylazo]benzenepropanamide [prepared from 8.19 g. (0.0316 mol) of 4-[2,2,2-trifluoro-1-hydroxy-1-trifluoromethyl)ethyl]benzenamine] and the partially saturated solution was heated on the steam bath for 3.5 hours with gentle stirring. The heterogeneous (NH₄Cl) reaction was concentrated under vacuum, mixed with water and ether and made basic with sodium bicarbonate. The ether layer was dried and concentrated with the addition of benzene to give 8.07 g. (63% overall from 4-[2,2,2-trifluoro-1-hydroxy-1-(trifluoromethyl)ethyl]benzenamine) of 3-phenyl-5-[2,2,2-trifluoro-1-hydroxy-1-(trifluoromethyl)ethyl]indole-2-carboxamide as colorless crystals, m.p. 227°–230°.

EXAMPLE 5

3-Phenyl-5-[2,2,2-trifluoro-1-hydroxy-1-(trifluoromethyl)ethyl]indole-2-carboxamide A solution of crude α-acetyl-α-[4-[2,2,2-trifluoro-1-hydroxy-1-(trifluoromethyl)ethyl]phenylazo]benzenepropanamide [prepared from 0.333 g. (1.3 mmol) of 4-[2,2,2-trifluoro-1-hydroxy-1-(trifluoromethyl)ethyl]benzenamine] in 10 ml. of hydrochloric acid and 10 ml. of acetic acid was allowed to stand at room temperature overnight and was then heated on the steam bath for 25 minutes. The reaction was mixed with water and ether and made basic with sodium bicarbonate. The ether layer was dried and concentrated with the addition of benzene to give 0.10 g. (19% overall from 4-[2,2,2-trifluoro-1-hydroxy-1-(trifluoromethyl)ethyl]benzenamine) of 3-phenyl-5-[2,2,2-trifluoro-1-hydroxy-1-(trifluoromethyl)ethyl]indole-2-carboxamide as colorless crystals, m.p. 220°–224°.

EXAMPLE 6

3-Phenyl-5-[2,2,2-trifluoro-1-hydroxy-1-(trifluoromethyl)ethyl]indole-2-carboxamide Hydrogen chloride was bubbled into a solution of 100 mg. (0.24 mmol) of α-[1-[4-[2,2,2-trifluoro-1-hydroxy-1(trifluoromethyl)ethyl]phenyl]hydrazin-2-ylidene]benzene propanamide in 20 ml. of ethanol and the reaction was heated on the steam bath for 2 hours and then concentrated under vacuum. The residue was diluted with sodium bicarbonate solution and extracted with ether. The ether layer was dried and concentrated with the addition of benzene to give 71 mg. (74%) of 3-phenyl-5-[2,2,2-trifluoro-1-hydroxy-1-(trifluoromethyl)ethyl]indole-2-carboxamide as tan crystals, m.p. 227°–228°.

EXAMPLE 7

3-Phenyl-5-[2,2,2-trifluoro-1-hydroxy-1-(trifluoromethyl)ethyl]indole-2-carbonitrile A homogeneous mixture of 19.7 g. (0.049 mol) of 3-phenyl-5-[2,2,2-trifluoro-1-hydroxy-1-(trifluoromethyl)ethyl]indole-2-carboxamide and 45.0 g. of phosphorus pentoxide was stirred and heated with an oil bath. After one hour at 180°–190° the dark purple viscous mixture was cooled, covered with ether, and the excess reagent was destroyed by the addition of water. The mixture was diluted with several liters of water and made slightly basic with sodium hydroxide. The ether layer and several ether extracts were combined, dried and concentrated. The residue was dissolved in 10% ether in benzene and passed over a column of 400 g. of silica gel made up in benzene. The eluates were concentrated and the crystalline residue was recrystallized from ether-dichloromethane to give 10.1 g. (54%) of 3-phenyl-5-[2,2,2-trifluoro-1-hydroxy-1-(trifluoromethyl)ethyl]indole-2-carbonitrile as colorless crystals, m.p. 251°–253°. The analytical sample was obtained from ether-tetrachloromethane as colorless crystals, m.p. 251°–253°.

Anal. Calcd for $C_{18}H_{10}F_6N_2O$: C, 56.26; H, 2.62; N, 7.29; F, 29.67. Found: C, 56.48; H, 2.64; N, 7.21; F, 29.66.

EXAMPLE 8

3-Phenyl-5-[2,2,2-trifluoro-1-hydroxy-1-(trifluoromethyl)ethyl]indole-2-carbonitrile A mixture of 0.50 g. (1.2 mmol) of 3-phenyl-5-[2,2,2-trifluoro-1-hydroxy-1-(trifluoromethyl)ethyl]indole-2-carboxamide and 1.0 g. of phosphorus pentoxide in 10 ml. of 1,1,2,2-tetrachloroethane was heated under reflux for 2 hours. The cooled reaction was treated with excess water, the aqueous layer was made slightly basic and the organic layer and several ether extracts were combined, dried and evaporated. The crystalline residue was recrystallized from ether-dichloromethane to give 0.20 g. (43%) of crude 3-phenyl-5-[2,2,2-trifluoro-1-hydroxy-1-(trifluoromethyl)ethyl]indole-2-carbonitrile as orange crystals, m.p. 247°–249°.

EXAMPLE 9

3-Phenyl-5-[2,2,2-trifluoro-1-hydroxy-1-(trifluoromethyl)ethyl]indole-2-carbonitrile A mixture of 0.50 g. (1.2 mmol) of 3-phenyl-5-[2,2,2-trifluoro-1-hydroxy-1-(trifluoromethyl)ethyl]indole-2-carboxamide, 0.28 g. of phosphorus pentoxide, 0.24 ml. of triethylamine and 5 ml. of benzene was heated under reflux for 48 hours. The cooled mixture was diluted with ether, washed with sodium bicarbonate solution and then with brine, dried and concentrated. The residue was recrystallized from ether-dichloromethane to give 0.20 g. (43%) of crude 3-phenyl-5-[2,2,2-trifluoro-1-hydroxy-1-(trifluoromethyl)ethyl]indole-2-carbonitrile as yellow crystals, m.p. 250°–253°.

EXAMPLE 10

3-Phenyl-5-[2,2,2-trifluoro-1-hydroxy-1-(trifluoromethyl)ethyl]indole-2-carbonitrile A mixture of 60.7 g. (0.15 mol) of 3-phenyl-5-[2,2,2-trifluoro-1-hydroxy-1-(trifluoromethyl)ethyl]indole-2-carboxamide and 400 g. of polyphosphate ester in 800 ml of chloroform was heated under reflux for 3.5 hours. The solvent was removed under vacuum and the residue was diluted with water, made slightly basic with sodium carbonate and extracted with ether. The ether extracts were dried and concentrated and the crystalline residue was recrystallized from ether-dichloromethane to give 48.2 g. (83%) of 3-phenyl-5-[2,2,2-trifluoro-1-hydroxy-1-(trifluoromethyl)ethyl]indole-2-carbonitrile as colorless crystals, m.p. 252°–254°.

EXAMPLE 11

3-Phenyl-5-[2,2,2-trifluoro-1-hydroxy-1-(trifluoromethyl)ethyl]indole-2-carbonitrile To 4.8 ml. of tetrahydrofuran cooled to 0° was added dropwise a solution of 0.26 ml. (0.45 g., 2.37 mmol) of titanium tetrachloride in 1.0 ml. of carbon tetrachloride. To the resulting orange solution was added dropwise a solution of 0.50 g. (1.2 mmol) of 3-phenyl-5-[2,2,2-trifluoro-1-hydroxy-1-(trifluoromethyl)ethyl]indole-2-carboxamide in 1.0 ml. of tetrahydrofuran. After the resulting deep brown solution was stirred at 0° for 10 minutes, 0.49 ml. of triethylamine was added and after stirring for an additional 8 hours at 0° stirring was continued at ambient temperature overnight. To the reaction was added 5 ml. of ether followed by 7 ml. of water. The organic phase and two ether extracts of the aqueous phase were combined, dried and concentrated. The resulting crystalline residue was recrystallized from ether-dichloromethane to give 0.20 g. (43%) of 3-phenyl-5-[2,2,2-trifluoro-1-hydroxy-1-(trifluoromethyl)ethyl]indole-2-carbonitrile was colorless crystals, m.p. 250°–253°.

EXAMPLE 12

3-Phenyl-5-[2,2,2-trifluoro-1-hydroxy-1-(trifluoromethyl)ethyl]indole-2-carbonitrile To the crude α-cyano-α-[4-[2,2,2-trifluoro-1-hydroxy-1-(trifluoromethyl)ethyl]phenylazo]benzenepropanoic acid ethyl ester prepared from 5.70 g. (0.022 mol) of 4-[2,2,2-trifluoro-1-hydroxy-1-(trifluoromethyl)ethyl]benzenamine was added 30 ml. of concentrated hydrochloric acid and 30 ml. of acetic acid. The solution was heated on the steam bath for 80 minutes, cooled, diluted with water, and extracted with ether.

The ether extracts were washed with sodium bicarbonate solution, dried over sodium sulfate, passed over a little silica gel and evaporated. The residue was recrystallized from ether-tetrachloromethane to give 1.60 g. (19%) of 3-phenyl-5-[2,2,2-trifluoro-1-hydroxy-1-(trifluoromethyl)ethyl]indole-2-carbonitrile as colorless crystals, m.p. 250°–253°.

EXAMPLE 13

3-Phenyl-5-[2,2,2-trifluoro-1-hydroxy-1-(trifluoromethyl)ethyl]indole-2-carbonitrile A mixture of 36.0 g. of polyphosphate ester and the crude α-cyano-α-[4-[2,2,2-trifluoro-1-hydroxy-1-(trifluoromethyl)ethyl]phenylazo]benzenepropanoic acid ethyl ester prepared from 7.0 g. (0.027 mol) of 4-[2,2,2-trifluoro-1-hydroxy-1-(trifluoromethyl)ethyl]benzenamine was heated on the steam bath for 2 hours, cooled, diluted with water, made basic with sodium bicarbonate and extracted with ether. The ether extracts were dried and concentrated. The crystalline residue was recrystallized from ether-tetrachloromethane to give 4.30 g. (41%) of 3-phenyl-5-[2,2,2-trifluoro-1-hydroxy-1-(trifluoromethyl)ethyl]indole-2-carbonitrile as colorless crystals, m.p. 249°–252°.

EXAMPLE 14

3-Phenyl-5-[2,2,2-trifluoro-1-hydroxy-1-(trifluoromethyl)ethyl]indole-2-carbonitrile A solution of 1.85 g. (4.60 mmol) of α-[1-[4-[2,2,2-trifluoro-1-hydroxy-1-(trifluoromethyl)ethyl]phenyl]hydrazin-2-ylidene]benzenepropanenitrile Isomer A in 30 ml. of acetic acid and 10 ml. of concentrated hydrochloric acid was stirred and gradually heated with an oil bath. After 30 minutes when the temperature was 35°, crystals of α-[1-[4-[2,2,2-trifluoro-1-hydroxy-1-(trifluoromethyl)ethyl]phenyl]hydrazin-2-ylidene]benzenepropanenitrile (Isomer B) had formed in the mixture which gradually dissolved on further heating. After the reaction had been heated to 70°–85° for 50 minutes it was concentrated under vacuum, mixed with sodium bicarbonate solution and extracted with ether. The ether was dried and evaporated to 1.50 g. of solid residue which upon recrystallization from ether-dichloromethane gave 0.93 g. (53%) of 3-phenyl-5-[2,2,2-trifluoro-1-hydroxy-1-(trifluoromethyl)ethyl]indole-2-carbonitrile as colorless crystals, m.p. 249°–251°.

EXAMPLE 15

3-Phenyl-5-[2,2,2-trifluoro-1-hydroxy-1-(trifluoromethyl)ethyl]indole-2-carbonitrile A slurry of 2.75 g. (0.0106 mol) of 4-[2,2,2-trifluoro-1-hydroxy-1-(trifluoromethyl)-ethyl]benzenamine in 4 ml. of concentrated hydrochloric acid and 7 ml. of water was kept below 5° while sodium nitrite was added until the reaction was homogeneous. This solution was then added to a mixture of 1.93 g. (0.011 mol) of α-cyanobenzenepropanoic acid and 20 ml. of ice water adjusted to pH 6 with sodium acetate. After stirring for 20 minutes at 0°–5°, the reaction was extracted with ether. The extracts were dried and concentrated and the resulting oil was mixed with 6 ml. of acetic acid and 6 ml. of concentrated hydrochloric acid and heated on the steam bath for 3 hours. The cooled reaction was diluted with water and extracted with ether. The extracts were dried and concentrated and the residue was recrystallized from ether-tetrachloromethane to give 0.435 g. (11%) of 3-phenyl-5-[2,2,2-trifluoro-1-hydroxy-1-(trifluoromethyl)ethyl]indole-2-carbonitrile, m.p. 248°–251°.

EXAMPLE 16

3-Phenyl-5-[2,2,2-trifluoro-1-hydroxy-1-(trifluoromethyl)ethyl]indole-2-carbonitrile A mixture of 8.80 g. (0.034 mol) of 4-[2,2,2-trifluoro-1-hydroxy-1-(trifluoromethyl)ethyl]benzenamine and 45 ml. of 4 N hydrochloric acid was maintained at 0°–5° while a solution of 2.40 g. (0.035 mol) of sodium nitrite in 10 ml. of water was slowly added. This solution was then added to a cold mixture of 7.00 g. (0.040 mol) of α-cyanobenzenepropanoic acid, 50 ml. of ethanol, 100 ml. of water and 15 ml. of 50% potassium hydroxide solution. Ten minutes later the reaction was extracted with ether and the ether was dried and evaporated. The residue was heated with 25 g. of polyphosphate ester to 190°, cooled, diluted with water and extracted with ether. The residue was crystallized from ether-hexane to give 2.20 g. (17%) of 3-phenyl-5-[2,2,2-trifluoro-1-hydroxy-1-(trifluoromethyl)ethyl]indole-2-carbonitrile as yellow crystals, m.p. 247°–250°.

EXAMPLE 17

α-Cyano-α-[4-[2,2,2-trifluoro-1-hydroxy-1-(trifluoromethyl)ethyl]phenylazo]benzene]propanoic acid ethyl ester To 30 ml. of 4 N hydrochloric acid was added 8.63 g. (0.033 mol) of 4-[2,2,2-trifluoro-1-hydroxy-1-(trifluoromethyl)ethyl]benzenamine, solution took place, followed by the formation of a fine precipitate of the hydrochloride of 4-[2,2,2-trifluoro-1-hydroxy-1-(trifluoromethyl)ethyl]benzenamine. This suspension was stirred and kept below 0° with an ice-salt bath while 2.53 g. (0.037 mol) of sodium nitrite was gradually added. Five minutes later 10.0 g. of sodium acetate was added followed by a solution of 6.70 g. (0.033 mol) of α-cyanobenzenepropanoic acid ethyl ester in 50 ml. of ethanol. After a further 30 minutes at 0°, the reaction was stirred another 20 minutes at ambient temperature, diluted with water and extracted with dichloromethane. The extracts were dried and concentrated to give 18.4 g. of a red oil of crude α-cyano-α-[4-[2,2,2-trifluoro-1-hydroxy-1-(trifluoromethyl)ethyl]phenylazo]benzenepropanoic acid ethyl ester. This crude material could be used as such, but on occasion was dissolved in benzene and passed over 200 g. of silica gel. Elution with increasing amounts of dichloromethane in benzene gave 15.3 g. (98%) of purified α-cyano-α-[4-[2,2,2-trifluoro-1-hydroxy-1-(trifluoromethyl)ethyl]phenylazo]benzenepropanoic acid ethyl ester as a yellow oil. After unsuccessful attempts to crystallize this material from various solvents including ether, excess solvents were removed under vacuum and the residual oil was found by analysis to contain one mole of ether, also seen in the nmr spectrum.

Anal. Calcd for $C_{21}H_{17}F_6N_3O_3 \cdot C_4H_{10}O$: C, 54.84; H, 4.97; N, 7.68; F, 20.82. Found: C, 55.27; H, 4.43; N, 8.14; F, 20.70.

EXAMPLE 18

α-[1-[4-[2,2,2-trifluoro-1-hydroxy-1-(trifluoromethyl)ethyl]phenyl]hydrazin-2-ylidene]benzenepropanenitrile Isomer A A solution of 238 mg. (0.5 mmol) of α-cyano-α-[4-[2,2,2-trifluoro-1-hydroxy-1-(trifluoromethyl)ethyl]- phenylazo]benzenepropanoic acid ethyl ester in 3 ml. of acetic acid and 1 ml. of concentrated hydrochloric acid was stirred at room temperature for 30 minutes, diluted with water, made basic with sodium bicarbonate and extracted with ether. The ether extracts were dried and concentrated. The residue was dissolved in 1:1 benzene-dichloromethane and passed over a little silica gel. The eluate was concentrated and crystallized from hexane to give α-[1-[4-[2,2,2-trifluoro-1-hydroxy-1-(trifluoromethyl)ethyl]phenyl]hydrazin-2-ylidene]benzenepropanenitrile Isomer A as yellow crystals, m.p. 90°–92°.

EXAMPLE 19

α-[1-[4-[2,2,2-trifluoro-1-hydroxy-1-(trifluoromethyl)ethyl]phenyl]hydrazin-2-ylidene]benzenepropanenitrile Isomer A To a suspension of 13.70 g. (0.053 mol) of 4-[2,2,2-trifluoro-1-hydroxy-1-(trifluoromethyl)ethyl]benzenamine in 48 ml. of 4 N hydrochloric acid stirred and kept at 0° or below was added gradually 3.66 g. (0.053 mol) of sodium nitrite, then 16.0 g. of sodium acetate, then a solution of 9.24 g. (0.053 mol) of α-cyanobenzenepropanoic acid and 4.40 g. of sodium acetate in 60 ml. of water. The solution was allowed to stand at ambient temperature for one hour during which an oil precipitated. The mixture was extracted with dichloromethane. The extract was dried and allowed to stand at room temperature during which gas was evolved and a small amount of precipitate formed. The solution was concentrated and the residue was put over 200 g. of silica gel in benzene. Elution with 30–80% dichloromethane in benzene gave fractions rich in α-[1-[4-[2,2,2-trifluoro-1-hydroxy-1-(trifluoromethyl)ethyl]phenyl]hydrazin-2-ylidene]benzenepropanenitrile Isomer A, while dichloromethane gave fractions rich in α-[1-[4-[2,2,2-trifluoro-1-hydroxy-1-(trifluoromethyl)ethyl]phenyl]hydrazin-2-ylidene]benzenepropanenitrile Isomer B (see Example 20). Recrystallization of the crude α-[1-[4-[2,2,2-trifluoro-1-hydroxy-1-(trifluoromethyl)ethyl]phenyl]hydrazin-2-ylidene]benzenepropanenitrile Isomer A from dichloromethane-hexane and then from hexane gave 3.71 g. (17.5%) of α-[1-[4-[2,2,2-trifluoro-1-hydroxy-1-(trifluoromethyl)ethyl]phenyl]hydrazin-2-yl-idene]benzenepropanenitrile Isomer A as pale yellow crystals, m.p. 90°–92°.

Anal. Calcd for $C_{18}H_{13}F_6N_3O$: C, 53.87; H, 3.27; F, 28.41; N, 10.47. Found: C, 53.89; H, 3.24; F, 28.57; N, 10.78.

EXAMPLE 20

α-[1-[4-[2,2,2-trifluoro-1-hydroxy-1-(trifluoromethyl)ethyl]phenyl]hydrazin-2-ylidene]benzenepropanenitrile Isomer B The fractions of crude α-[1-[4-[2,2,2-trifluoro-1-hydroxy-1-(trifluoromethyl)ethyl]phenyl]hydrazin-2-ylidene]benzenepropanenitrile Isomer B obtained in Example 19 were recrystallized from ether-hexane to give 0.76 g. (4) of α-[1-[4-[2,2,2-trifluoro-1-hydroxy-1-(trifluoromethyl)ethyl]phenyl]hydrazin-2-ylidene]benzenepropanenitrile Isomer B as colorless crystals, m.p. 164.5°–167°.

EXAMPLE 21

α-[1-[4-[2,2,2-trifluoro-1-hydroxy-1-(trifluoromethyl)ethyl]phenyl]hydrazin-2-ylidene]benzenepropanenitrile Isomer B A solution of 1.25 g. (3.1 mmol) of α-[1-[4-[2,2,2-trifluoro-1-hydroxy-1-(trifluoromethyl)ethyl]phenyl]hydrazin-2-ylidene]benzenepropanenitrile Isomer A in 15 ml. of acetic acid and 5 ml. of concentrated hydrochloric acid was gradually warmed over 15 minutes to 35° with an oil bath. The resulting precipitate was recrystallized from dichloromethane-hexane to give 0.48 g. (40%) of α-[1-[4-[2,2,2-trifluoro-1-hydroxy-1-(trifluoromethyl)ethyl]phenyl]hydrazin-2-ylidene]benzenepropanenitrile Isomer B as colorless crystals, m.p. 164.5°–166.5°. Further recrystallization from benzene gave the analytical sample, m.p. 165°–167°.

Anal. Calcd for $C_{18}H_{13}F_6N_3O$: C, 53.87; H, 3.27; F, 28.41; N, 10.47. Found: C, 53.92; H, 3.28; F, 28.25; N, 10.51.

EXAMPLE 22

3-Phenylindole-2-carbonitrile

A solution of 4.08 g. (0.044 mol) of aniline in 18 ml. of concentrated hydrochloric acid and 50 ml. of water was maintained below 5° while a solution of 3.00 g. (0.043 mol) of sodium nitrite in 10 ml. of water was added. This solution was then added to a mixture of 8.30 g. (0.041 mol) of α-cyanobenzenepropanoic acid ethyl ester, 50 ml. of ethanol, 100 ml. of water, and 18 ml. of 50% potassium hydroxide solution maintained below 0°. After stirring for an additional 20 minutes the reaction was diluted with water and shaken with ether. Some insoluble solid was removed by filtration and the ether layer was concentrated. The residue was heated on the steam bath for 4 hours with 60 ml. of acetic acid and 60 ml. of concentrated hydrochloric acid. The cooled reaction was diluted with water and extracted with dichloromethane. The extracts were dried, filtered over some silica gel and concentrated. Recrystallization of the residue from dichloromethane-hexane gave 3-phenylindole-2-carbonitrile as tan crystals, m.p. 137°–142°.

EXAMPLE 23

5-Chloro-3-phenylindole-2-carbonitrile

A mixture of 5.40 g. (0.42 mol) of 4-chloroaniline, 18 ml. of concentrated hydrochloric acid and 50 ml. of water was stirred and maintained below 5° while a solution of 3.00 g. (0.043 mol) of sodium nitrite in 10 ml. of water was added and until the reaction became homogeneous. It was then added to a 0° mixture of 8.70 g. (0.43 mol) of α-cyanobenzenepropanoic acid ethyl ester, 50 ml. of ethanol, 100 ml. of water and 18 ml. of 50% potassium hydroxide solution. After a further 20 minutes at 0° the reaction was diluted with water and extracted with ether. The extracts were dried and concentrated and the residue was mixed with 30 ml. of acetic acid and 30 ml. of concentrated hydrochloric acid. A precipitate formed rapidly and after the mixture was heated on the steam bath for 30 minutes was collected by filtration from the cooled reaction. The filtrate was diluted with water and extracted with ether. The solid was dissolved in these extracts, the solution was dried and concentrated and the residue was passed over a column of silica gel in dichloromethane. The residue obtained on concentration of the eluates was recrystallized from dichloromethane-ether-hexane to give 6.0 g. (57%) of 5-chloro-3-phenylindole-2-carbonitrile as colorless crystals, m.p. 115°–117°.

EXAMPLE 24

α-[1-(4-Nitrophenyl)hydrazin-2-ylidene]benzenepropanenitrile and 5-Nitro-3-phenylindole-2-carbonitrile A solution of 3.00 g. (0.043 mol) of sodium nitrite in 10 ml. of water was added to a 5° mixture of 5.85 g. (0.042 mol) of 4-nitroaniline, 18 ml. of concentrated hydrochloric acid and 50 ml. of water. After stirring for one hour the (slightly heterogeneous) reaction was added to a 0° mixture of 8.70 g. (0.43 mol) of α-cyanobenzenepropanoic acid ethyl ester, 50 ml. of ethanol, 100 ml. of water and 18 ml. of 50% potassium hydroxide solution. The reaction became purple, then green, then yellow and finally deposited a yellow gummy solid. This was dissolved in 15 ml. of concentrated hydrochloric acid and 15 ml. of acetic acid and heated under reflux for 2 hours. The cooled (homogeneous) reaction mixture was diluted with water to force out 5.50 g. of a gummy-ether insoluble-solid. The aqueous solution on standing at room temperature for 3 days deposited 600 mg. of α-[1-(4-nitrophenyl)hydrazin-2-ylidene]benzenepropanenitrile as yellow crystals, m.p. 158°–160°. The original 5.5 g. of solid was slurried with benzene onto a column of silica gel. Elution with 2–7% dichloromethane in benzene gave further amounts of α-[1-(4-nitrophenyl)hydrazin-2-ylidene]benzenepropanenitrile, while elution with 40% dichloromethane in benzene to 2% ether in dichloromethane gave 5-nitro-3-phenylindole-2-carbonitrile as yellow crystals, m.p. 258°–262°, after washing with ether.

EXAMPLE 25

5-Nitro-3-phenylindole-2-carbonitrile

A suspension of 600 mg. (2.15 mmol) of α-[1-(4-nitrophenyl)hydrazin-2-ylidene]benzenepropanenitrile in 3 ml. of concentrated hydrochloric acid and 3 ml. of acetic acid was heated on the steam bath for 6 hours. The reaction remained heterogeneous throughout and was complete by tlc. The cooled reaction was filtered, and the solid was washed with hexane, to give 520 mg. (92%) of crude 5-nitro-3-phenylindole-2-carbonitrile as yellow crystals, m.p. 242°–254°.

EXAMPLE 26

2-Cyano-3-phenylindole-5-carboxylic acid methyl ester

A suspension of 13.7 g. (0.10 mol) of 4-aminobenzoic acid in 90 ml. of 4 N hydrochloric acid was maintained below 0° and stirred while 7.55 g. (0.016 mol) of sodium nitrite was added. The excess hydrochloric acid was destroyed by the addition of 30.0 g. of sodium acetate and then a solution of 20.3 g. (0.10 mol) of α-cyanobenzenepropanoic acid ethyl ester in 50 ml. of ethanol was added. The reaction was allowed to warm to room temperature and then diluted with water and extracted with dichloromethane. The extract was dried and concentrated to leave 41 g. of an orange oil which was dissolved in 300 ml. of acetic acid and 100 ml. of concentrated hydrochloric acid. This solution was gradually heated with an oil bath and at about 65° gas evolution commenced. The reaction was kept at 70°, after 1.5 hours gas evolution had stopped, after 2.5 hours the reaction was heterogeneous and after 3.5 hours, it was cooled and filtered. The filtrate was concentrated under vacuum and the residue was mixed with water and dichloromethane. The resulting solid (of impure 2-cyano-3-phenylindole-5-carboxylic acid) was mixed with the original solid, total weight 21.2 g., and suspended in 200 ml. of methanol. The methanol was then saturated with hydrogen chloride and heated under reflux for 6 hours. The methanol was removed under vacuum and the residue was heated with benzene. The benzene insoluble solid was recrystallized repeatedly from methanol with charcoal, filtered over silica gel in ethyl acetate and recrystallized from methanol again to give 2.20 g. (8%) of 2-cyano-3-phenylindole-5-carboxylic acid methyl ester as colorless crystals, m.p. 250°–253°.

Anal. Calcd for $C_{17}H_{12}N_2O_2$: C, 73.90; H, 4.38; N, 10.14. Found: C, 74.03; H, 4.40; N, 10.22.

EXAMPLE 27

2-Cyano-3-phenylindole-5-carboxylic acid

A suspension of 1.50 g. (5.4 mmol) of 2-cyano-3-phenylindole-5-carboxylic acid methyl ester in 50 ml. of 6 N hydrochloric acid was heated under reflux, enough ethanol (~ 100 ml.) was added to effect solution, and heating was continued for 11 days. The reaction was concentrated to a small volume under vacuum, diluted with water and made basic with sodium hydroxide. Filtration gave 840 mg. of recovered 2-cyano-3-phenylindole-5-carboxylic acid methyl ester. The basic solution was acidified, the amorphous precipitate was collected by filtration and recrystallized four times from methanol with charcoal to give 111 mg. (19%) of 2-cyano-3-phenylindole-2-carboxylic acid as colorless crystals, m.p. 302°–304°.

Anal. Calcd for $C_{16}H_{10}N_2O_2$: C, 73.27; H, 3.84; N, 10.68. Found: C, 73.00; H, 4.01; N, 10.48.

EXAMPLE 28

α-acetyl-α-[4-[2,2,2-trifluoro-1-hydroxy-1-(trifluoromethyl)ethyl]phenylazo]benzenepropanamide A mixture of 10.4 g. (0.04 mol) of 4-[2,2,2-trifluoro-1-hydroxy-1-(trifluoromethyl)-ethyl]benzenamine and 36 ml. of 4 N hydrochloric acid was maintained at 2° or below while a solution of 2.76 g. (0.04 mol) of sodium nitrite in 10 ml. of water was added. The reaction was stirred for an additional 30 minutes in the ice bath, 12.0 g. of sodium acetate was added, followed by a slurry of 7.65 g. (0.04 mol) of α-acetylbenzenepropanamide in 50 ml. of ethanol. The cooling bath was removed; after 30 minutes, when the temperature was 6°, 50 ml. of methanol was added and the resulting solution was stirred an additional 80 minutes at ambient temperature. The reaction was diluted with water and extracted with dichloromethane. The extracts were dried over sodium sulfate, passed over a small amount of silica gel and concentrated under vacuum to give 19.28 g. of crude α-acetyl-α-[4-[2,2,2-trifluoro-1-hydroxy-1-(trifluoromethyl)ethyl]phenylazo]benzenepropanamide as an orange oil which gradually crystallized. This material was recrystallized only with difficulty and was generally used as is for subsequent reactions. An analytical sample was prepared by repeated solution in dichloromethane, dilution with tetrachloromethane and slow evaporation of the dichloromethane to give α-acetyl-α-[4-[2,2,2-trifluoro-1-hydroxy-1-(trifluoromethyl)ethyl]phenylazo]benzenepropanamide as yellow crystals, m.p. 128°–133°.

Anal. Calcd for $C_{20}H_{17}F_6N_3O_3$: C, 52.06; H, 3.71; F, 24.71; N, 9.11. Found: C, 52.27; H, 3.79; F, 24.45; N, 9.24.

EXAMPLE 29

α-[1-[4-[2,2,2-trifluoro-1-hydroxy-1-(trifluoromethyl)ethyl]phenyl]hydrazin-2-ylidene]benzenepropanamide To a slurry of 5.20 g. (0.02 mol) of 4-[2,2,2-trifluoro-1-hydroxy-1-(trifluoromethyl)ethyl]benzenamine in 18 ml. of 4 N hydrochloric acid cooled to 5° was added with stirring a solution of 1.38 g. (0.02 mol) of sodium nitrite in 4 ml. of water. After the reaction had been stirred for an additional 45 minutes, 6.0 g. of sodium acetate was added followed by a solution of 3.86 g. (0.02 mol) of α-(aminocarbonyl)benzenepropanoic acid in 30 ml. of water containing sufficient sodium acetate to effect solution. After stirring at ambient temperature for 2 hours, the reaction was extracted with dichloromethane. The extracts were allowed to stand at room temperature overnight, filtered through a filter aid, and concentrated under vacuum to leave an oil. Recrystallization from ether-benzene gave 701 mg. (8%) of the analytical sample of α-[1-[4-[2,2,2-trifluoro-1-hydroxy-1-(trifluoromethyl)ethyl]phenyl]hydrazin-2-ylidene]benzenepropanamide as cream crystals, m.p. 211°-213°.

Anal. Calcd. for $C_{18}H_{15}F_6N_3O_2$: C, 51.55; H, 3.61; F, 27.19; N, 10.02. Found: C, 51.76; H, 3.80; F, 27.16; N, 9.98.

EXAMPLE 30

α-[1-[4-[2,2,2-trifluoro-1-hydroxy-1-(trifluoromethyl)ethyl]phenyl]hydrazin-2-ylidene]benzenepropanamide Hydrogen chloride was bubbled into a solution of crude α-acetyl-α-[4-[2,2,2-trifluoro-1-hydroxy-1-(trifluoromethyl)ethyl]phenylazo]benzenepropanamide [prepared from 1.00 g. (3.9 mmol) of 4-[2,2,2-trifluoro-1-hydroxy-1-(trifluoromethyl)ethyl]benzenamine] in 25 ml. of ethanol and the reaction was allowed to stand at ambient temperature for 3 hours. The solution was concentrated under vacuum at room temperature and the residue was mixed with sodium bicarbonate solution and extracted with ether. The ether layer was dried and concentrated with the addition of benzene to give 0.68 g. (75%) of α-[1-[4-[2,2,2-trifluoro-1-hydroxy-1-(trifluoromethyl)ethyl]phenyl]hydrazin-2-ylidene]benzenepropanamide as cream crystals, m.p. 210°-212°.

EXAMPLE 31

2-Methyl-3-oxo-2-[4-[2,2,2-trifluoro-1-hydroxy-1-(trifluoromethyl)ethyl]phenylazo]butanamide To 15.8 ml. of 3 N hydrochloric acid was added 4.56 g. (0.0176 mol) of 4-[2,2,2-trifluoro-1-hydroxy-1-(trifluoromethyl)ethyl]benzenamine, the reaction was cooled to 0°, and a solution of 1.212 g. (0.176 mol) of sodium nitrite in 5 ml. of water was slowly added. After the reaction was stirred for an additional 30 minutes, 5.25 g. of sodium acetate was added followed by a solution of 1.850 g. (0.016 mol) of 2-methyl-3-oxobutanamide in 10 ml. of methanol. The resulting yellow solution soon became heterogeneous and was allowed to warm to 18° over a two hour period. The solid was collected by filtration, washed with water and dissolved in ether. The ether layer was dried and concentrated with the addition of dichloromethane to give 5.65 g. (91%) of 2-methyl-3-oxo-2-[4-[2,2,2-trifluoro-1-hydroxy-1-(trifluoromethyl)ethyl]phenylazo]butanamide as yellow crystals, m.p. 148.5°-151.5°. Further recrystallization gave the analytical sample, m.p. 149°-151°.

Anal. Calcd for $C_{14}H_{13}F_6N_3O_3$: C, 43.64; H, 3.40; F, 29.59; N, 10.91. Found: C, 43.68; H, 3.35; F, 29.37; N, 10.99.

EXAMPLE 32

2-[1-[4-[2,2,2-Trifluoro-1-hydroxy-1-(trifluoromethyl)ethyl]phenyl]hydrazin-2-ylidene]propanamide Hydrogen chloride was passed into a solution of 26.8 g. (0.070 mol) of 2-methyl-3-oxo-2-[4-[2,2,2-trifluoro-1-hydroxy-1-(trifluoromethyl)ethyl]phenylazo]butanamide in 300 ml. of ethanol until the original gold color had changed to pale yellow and the solution had become just barely warm. The ethanol was removed at room temperature under vacuum, and the resulting solid was slurried with ether and filtered to give 17.0 g. of 2-[1-[4-[2,2,2-trifluoro-1-hydroxy-1-(trifluoromethyl)ethyl]phenyl]hydrazine-2-ylidene]propanamide as very pale yellow, ether-insoluble crystals, m.p. 212°-213.5°, after turning colorless at 170°. When this solid was heated enough with ether to effect solution, it was converted into a colorless rather-more-readily ether soluble solid which after recrystallization from ether-dichloromethane had m.p. 213.5°-215°.

Anal. Calcd for $C_{12}H_{11}F_6N_3O_2$: C, 41.99; H, 3.23; F, 33.21; N, 12.24. Found: C, 42.10; H, 3.40; F, 33.27; N, 12.30.

Concentration of the original ether mother liquor with the addition of dichloromethane gave additional material of comparable m.p. for a total yield of 22.42 g. (94%).

EXAMPLE 33

2-[1-[4-[2,2,2-Trifluoro-1-hydroxy-1-(trifluoromethyl)ethyl]phenyl]hydrazin-2-ylidene]propanoic acid ethyl ester Isomer A A solution of 250 mg. (0.73 mmol) of 2-[1-[4-[2,2,2-trifluoro-1-hydroxy-1-(trifluoromethyl)ethyl]phenyl]hydrazin-2-ylidene]propanamide in ethanol containing some hydrogen chloride was heated under reflux for 10 hours and then concentrated under vacuum. The residue was mixed with ether and filtered to remove just a little unreacted 2-[1-[4-[2,2,2-trifluoro-1-hydroxy-1-(trifluoromethyl)ethyl]phenyl]hydrazin-2-ylidene]propanamide. The filtrate was concentrated and the resulting yellow oil was scratched with benzene. The resulting solid was recrystallized twice from ether-benzene to give 45 mg. (17%) of 2-[1-[4-[2,2,2-trifluoro-1-hydroxy-1-(trifluoromethyl)ethyl]phenyl]hydrazin-2-ylidene]propanoic acid ethyl ester Isomer A as pale yellow crystals, m.p. 167°-168.5° undepressed on mixing with a sample prepared in Example 34.

EXAMPLE 34

2-[1-[4-[2,2,2-Trifluoro-1-hydroxy-1-(trifluoromethyl)ethyl]phenyl]hydrazin-2-ylidene]propanoic acid ethyl ester Isomer A To 90 ml. of 3 N hydrochloric acid was added 25.9 g. (0.10 mol) of 4-[2,2,2-trifluoro-1-hydroxy-1-(trifluoromethyl)ethyl]benzenamine, the reaction was cooled to 0° and a solution of 6.88 g. (0.10 mol) of sodium nitrite in 30 ml. of water was slowly added. After the reaction was stirred for an additional 30 minutes, 30.0 g. of sodium acetate was added followed by a solution of 14.42 g. (0.10 mol) of 2-methyl-3-oxobutanoic acid ethyl ester in 50 ml. of methanol. The reaction was stirred at room temperature overnight and extracted with ether. The ether layer was washed with sodium bicarbonate solution, dried and concentrated. The resulting solid was recrystallized from ether-dichloromethane to give 11.32 g. (30%) of 2-[1-[4-[2,2,2-trifluoro-1-hydroxy-1-(trifluoromethyl)ethyl]phenyl]hydrazin-2-ylidene]propanoic acid ethyl ester Isomer A as yellow crystals, m.p. 168°–170°. The analytical sample had m.p. 169°–171°.

Anal. Calcd for $C_{14}H_{14}F_6N_2O_3$: C, 45.17; H, 3.79; F, 30.62; N, 7.56. Found: C, 45.09; H, 3.69; F, 30.61; N, 7.68.

EXAMPLE 35

2-[1-[4-[2,2,2-Trifluoro-1-hydroxy-1-(trifluoromethyl)ethyl]phenyl]hydrazin-2-ylidenepropanoic acid ethyl ester Isomer B The mother liquors of a sample of 2-[1-[4-[2,2,2-trifluoro-1-hydroxy-1-(trifluoromethyl)ethyl]phenyl]hydrazin-2-ylidene]propanoic acid ethyl ester Isomer A prepared from 2-[1-[4-[2,2,2-trifluoro-1-hydroxy-1-(trifluoromethyl)ethyl]phenyl]hydrazin-2-ylidene]-propanamide were concentrated and passed over a silica gel column in dichloromethane solution. The first eluted material was 2-[1-[4-[2,2,2-trifluoro-1-hydroxy-1-(trifluoromethyl)ethyl]phenyl]hydrazin-2-ylidene]-propanoic acid ethyl ester Isomer B isolated and analyzed as a pale yellow oil but which subsequently crystallized and which, after recrystallization from hexane, had m.p. 67°–69°.

Anal. Calcd for $C_{14}H_{14}F_6N_2O_2$: C, 45.17; H, 3.79; F, 30.62; N, 7.56. Found: C, 45.44; H, 3.94; F, 30.74; N, 7.68.

EXAMPLE 36

3,6-Dimethyl-2-[4-[2,2,2-trifluoro-1-hydroxy-1-(trifluoromethyl)ethyl]phenyl]-2H-1,2,4-triazin-5-one A mixture of 10.00 g. (0.029 mol) of 2-[1-[4-[2,2,2-trifluoro-1-hydroxy-1-(trifluoromethyl)ethyl]phenyl]hydrazin-2-ylidene]propanamide, 50 ml. of acetic acid and 10.0 ml. of boron trifluoride-etherate was heated on the steam bath for 40 hours and then concentrated under vacuum. The residue was shaken with 400 ml. of ether and filtered through a bed of a filter-aid. The filtrate was washed with aqueous sodium bicarbonate, dried and evaporated. Trituration with a little ether gave some solid which after recrystallization from methanol-ethyl acetate gave 3.00 g. (28%) of 3,6-dimethyl-2-[4-[2,2,2-trifluoro-1-hydroxy-1-(trifluoromethyl)ethyl]-phenyl]-2H-1,2,4-triazin-5-one as colorless crystals, m.p. 264°–266°. The analytical sample had m.p. 265°–266°.

Anal. Calcd for $C_{14}H_{11}F_6N_3O_2$: C, 45.78; H, 3.02; F, 31.04; N, 11.44. Found: C, 45.93; H, 3.17; F, 31.28; N, 11.52.

EXAMPLE 37

5-[2,2,2-Trifluoro-1-hydroxy-1-(trifluoromethyl)ethyl]indole-2-carboxamide

A mixture of 10.00 g. (0.029 mol) of 2-[1-[4-[2,2,2-trifluoro-1-hydroxy-1-(trifluoromethyl)ethyl]phenyl]hydrazin-2-ylidene]propanamide and 50 g. of zinc chloride was stirred and heated with an oil bath at 145° for 6 hours. The reaction was allowed to cool somewhat, mixed with 1 N hydrochloric acid and extracted with ether. The extracts were washed with 0.5 N hydrochloric acid and with water, dried and concentrated. The residue was recrystallized from ether-dichloromethane, passed over some silica gel in ether and recrystallized again to give 3.76 g. (40%) of 5-[2,2,2-trifluoro-1-hydroxy-1-(trifluoromethyl)ethyl]indole-2-carboxamide as cream crystals, m.p. 264°–266.5°. The analytical sample had m.p. 263°–266°.

Anal. Calcd for $C_{12}H_8F_6N_2O_2$: C, 44.18; H, 2.47; F, 34.95; N, 8.59. Found: C, 44.16; H, 2.44; F, 35.03; N, 8.54.

Similar results were obtained at 165° (3 hours reaction) and at 185° (one hour reaction).

EXAMPLE 38

5-[2,2,2-Trifluoro-1-hydroxy-1-(trifluoromethyl)ethyl]indole-2-carboxamide

The ether triturate mother liquor from the preparation of 3,6-dimethyl-2-[4-[2,2,2-trifluoro-1-hydroxy-1-(trifluoromethyl)ethyl]phenyl]-2H-1,2,4-triazin-5-one was concentrated with the addition of dichloromethane to give a 12% yield of 5-[2,2,2-trifluoro-1-hydroxy-1-(trifluoromethyl)ethyl]indole-2-carboxamide, m.p. 262°–263°.

EXAMPLE 39

5-[2,2,2-Trifluoro-1-hydroxy-1-(trifluoromethyl)ethyl]indole-2-carbonitrile

A solution of 8.50 g. (0.026 mol) of 5-[2,2,2-trifluoro-1-hydroxy-1-(trifluoromethyl)ethyl]indole-2-carboxamide in 100 ml. of chloroform and 100 ml. of an ether-chloroform solution of polyphosphate ester was heated under reflux for 45 minutes and concentrated under vacuum. The residue was mixed with ether and water and made basic with sodium bicarbonate. The ether layer was then dried and concentrated, and the residue was mixed with dichloromethane. Filtration removed a little starting material and concentration gave several crops of crude 5-[2,2,2-trifluoro-1-hydroxy-1-(trifluoromethyl)ethyl]indole-2-carbonitrile. The mother liquors were absorbed on silica gel from benzene solution. Elution with 0–10% ether in dichloromethane gave further 5-[2,2,2-trifluoro-1-hydroxy-1-(trifluoromethyl)ethyl]indole-2-carbonitrile. Recrystallization of the combined material from dichloromethane gave 5.60 g. (70%) of 5-[2,2,2-trifluoro-1-hydroxy-1-(trifluoromethyl)ethyl]indole-2-carbonitrile as colorless crystals, m.p. 183°–185°. The analytical sample had m.p. 181°–184°.

Anal. Calcd for $C_{12}H_6F_6N_2O$: C, 46.76; H, 1.96; F, 36.99; N, 9.09. Found: C, 46.45; H, 2.15; F, 36.51; N, 8.92.

The following examples illustrate the prostaglandin inhibitory activity of compounds within the scope of this invention.

The indoles tested herein are referred to as the "nitrile" and the "amide".

EXAMPLE 40

Arachidonic Acid Diarrhea Prevention

Carworth Farm CF-1 male mice weighing 18–20 grams were administered the test compound by either the oral or intraperitoneal route one hour prior to the intraperitoneal administration of 4 mg/kg of arachidonic acid (Hoffmann-La Roche Inc.). A stock solution (0.8 ml.) containing 25 mg. of arachidonic acid per milliliter of benzene was diluted with 0.08 ml. of 95% ethanol; ground together with 50 mg. of dry gum acacia with a mortar and pestle; and brought to a volume of 5 ml. with distilled water. A dose of 4 mg/kg of arachidonic acid produced a diarrhea graded 1 to 4+intensity in all mice. The diarrhea was graded on paper towels as follows: 0=solid pellet or no bowel movement; 1=slightly soft pellet with little or no wet ring formation; 2=moderately soft pellet with definite wet ring formation; 3=soft pellet with large wet ring formation; and 4=amorphous pellet with very large wet ring formation.

The $ED_{50}$ was the dose which reduced the expected diarrhea score of six pretreated mice by 50% compared to the total diarrhea score of six control mice thirty minutes after arachidonic acid administration. The calculation of the $ED_{50}$ was made according to the method of Miller et al., *Proc. Soc. Exp. Biol. Med.*, 57, pages 261–264 (1944).

The results are tabulated in Table 1, column a.

EXAMPLE 41

Inhibition of Prostaglandin Formation

Male rats, 5 per group, weighing approximately 200 grams were given various doses (up to 100 mg/kg) of test compounds orally by intubation and sacrificed after one hour at which time blood was collected and serum prepared. The serum samples were extracted with ethyl acetate. Aliquots of the extracts were evaporated under nitrogen and assayed for prostaglandin-like activity by radioimmunoassay employing antibodies raised to $PGF_{2\alpha}$ in rabbits. The percent inhibition value was plotted against log dose and a value for 50% inhibition was obtained by inspection.

The results are shown in Table 1, column b and Table 2.

EXAMPLE 42

Inhibition of Platelet Aggregation

Venous blood was collected from human volunteers in siliconized 20 ml. Vacutainer tubes (Becton & Dickinson & Co., Rutherford, N.J.) fitted with 20-gauge needles using 3.8% sodium citrate as the anticoagulant (9 parts of blood to 1 part of sodium citrate solution). Platelet rich plasma (PRP) was separated from the red blood cells by centrifugation at 180×g for 15 minutes at room temperature. Platelet poor plasma (PPP) was prepared by centrifuging PRP at 1000×g for 2 minutes.

Techniques established by Born et al., *J. Physiol.* (London), 168, pages 178–195 (1963) were used to study platelet aggregation in vitro employing a Payton Dual Channel Aggregation Module (Payton Associates, Inc., Buffalo, N.Y.). PRP (1 ml.) was added to a siliconized cuvette containing a siliconized stirring bar and placed in a densitometer maintained at 37° C. and stirred at 1000 RPM. Various concentrations of test compounds were added in 50 μl of saline and incubated with PRP for 5 minutes. Aggregation was initiated by the addition of sufficient concentrations of ADP (Sigma Chemical Co.), epinephrine HCl (Parke, Davis & Co., Detroit, Michigan), or human mammary gland collagen (obtained from Roosevelt Hospital, N.Y.) to give about 60% of maximum aggregation response. The light transmission through PPP was used to determine maximum response. The percent inhibition of aggregation caused by the drug was calculated from the strip chart recordings at the point of maximum collagen response. The percent inhibition value (Table 3) thus obtained was plotted against log concentration and a value for 50% inhibition was extrapolated from the graph.

The results are expressed as $IC_{50}$ (μM) in Table 4A and Table 7.

EXAMPLE 43

Effect of Compounds in Whole Blood

Aliquots of citrated human blood (10 ml.) were exposed to different concentrations of the "nitrile" by mechanically shaking at room temperature for 5 minutes. Platelet rich plasma was prepared and tested for inhibition of collagen-induced platelet aggregation as described in Example 42.

The results are tabulated in Table 4B and Table 5.

EXAMPLE 44

Prostaglandin Synthetase Inhibition

Prostaglandin synthetase activity in the presence and absence of the "nitrile" was determined, Smith et al., *J. Biol. Chem.*, 246, pages 6700–6704 (1971).

The results are tabulated in Table 1, column c.

EXAMPLE 45

Acute Toxicity in Mice

CF-IS mice of both sexes weighing 17–25 grams were used. The compounds were ground in a mortar and suspended in 5% gum acacia for oral or intraperitoneal administration. Eight to ten mice were used per dose level. The animals were observed for five days and total mortality reported. The $LD_{50}$ was calculated by the method of Miller et al., *Proc. Soc. Exp. Biol. Med.*, 57, pages 261–264 (1944).

The results are tabulated in Table 6, column a.

EXAMPLE 46

Gastric Ulcer Induction

The test is a modification of that described by Brodie et al., *Gastroenterology*, 53, pages 604–610 (1967). Male Wistar rats (Royal Hart Laboratories) were deprived of food for 18 hours prior to testing. Tap water was permitted ad libitum. Test compounds were administered orally four hours to autopsy. The rats were sacrificed under ethyl ether anesthesia, opened along the ventral midline and the stomachs removed. The stomach was divided along the lesser curvature, everted, rinsed in saline, and examined for the presence of focal hemorrhage. Ulcers were rated on an all or none basis for incidence and, in addition, each stomach is graded for severity of ulcers formed. Ulcer scores: 0=none, 1=trace, 2=mild, 3=moderate, and 4=severe. The results of the ulcer scores obtained were subjected to statistical analysis by the student 't' test.

The results are tabulated in Table 6, column b.

Table 1

| | Effect of prostaglandin synthesis inhibitors experimental prostaglandin systems | | |
|---|---|---|---|
| | (a) arachidonic acid induced diarrhea $ED_{50}$ mg/kg p.o. | (b) serum $PGF_{2\alpha}$ $ED_{50}$/mg/kg p.o. i.p. | (c) PG synthetase $IC_{50}$ [μM] |
| "nitrile" | 5.0 | 10  15 | 0.5 |
| Aspirin | 1.3 | 10  10 | 400 |
| Indomethacin | 0.8 | 1  <1 | 1.0 |

Table 2

Effect of "nitrile" on serum prostaglandin levels

| Dose mg/kg | PGF$_{2\alpha}$ ng/ml ± SE p.o. | PGF$_{2\alpha}$ ng/ml ± SE i.p. |
|---|---|---|
| 0 | 26 ± 1.4 | 26 ± 1.6 |
| 1 | 28 ± 4.6 | 27 ± 2.9 |
| 3 | 19 ± 4.2 | 18 ± 1.5[a] |
| 10 | 12 ± 2.4[c] | 18 ± 2.9[b] |
| 30 | 0 | 2 ± 1.6[c] |
| 100 | 0 | 0 |

[a] $p < 0.05$
[b] $p < 0.01$
[c] $p < 0.001$

Table 3

Inhibition of platelet aggregation in human plasma by "nitrile"

| Drug conc (µM) | Collagen induced aggregation Expt. I Δ light transmission units | Collagen induced aggregation Expt. I Percent Inhibition | Collagen induced aggregation Expt. II Δ light transmission units | Collagen induced aggregation Expt. II percent Inhibition |
|---|---|---|---|---|
| 0 | 65 | — | 60 | — |
| 50 | 4 | 93.8 | 3 | 95.0 |
| 25 | 5 | 92.4 | 5 | 91.6 |
| 15 | 8 | 87.7 | 7 | 88.3 |
| 5. | 24 | 63.1 | 20 | 66.6 |
| 2.5 | 49 | 24.6 | 50 | 16.7 |

| Drug conc (µM) | ADP induced aggregation (second wave) Δ light transmission units | Percent Inhibition | Δ light transmission units | Percent Inhibition |
|---|---|---|---|---|
| 0 | 60 | — | 55 | — |
| 50 | 0 | 100 | 0 | 100 |
| 20 | 0 | 100 | 0 | 100 |
| 10 | 11 | 18.6 | 14 | 74.5 |
| 5 | 50 | 16.7 | 44 | 20.0 |
| 2.5 | 60 | 0 | 54 | 1.8 |

| Drug conc (µM) | Epinephrine induced aggregation (second wave) Δ light transmission units | Percent Inhibition | Δ light transmission units | Percent Inhibition |
|---|---|---|---|---|
| 0 | 45 | — | 50 | — |
| 100 | 11 | 75.0 | 9 | 82.0 |
| 50 | 18 | 60.0 | 14 | 71.0 |
| 25 | 25 | 44.4 | 30 | 40.0 |
| 20 | 30 | 33.3 | 34 | 32.0 |
| 10 | 45 | 0 | 47 | 6.0 |

Table 4

Summary of "Nitrile" Data on Platelet Aggregation in Human Citrated Platelet-Rich Plasma A. Incubation of drugs in platelet-rich plasma

| | IC$_{50}$[µM] collagen | ADP | epinephrine |
|---|---|---|---|
| "nitrile" | 3.5 | 7.0 | 40 |
| Aspirin | 30.0 | 30.0 | 17 |
| Indomethacin | 1.0 | 0.1 | 2 |

B. Incubation of drugs in whole blood

| | IC$_{50}$ [µM] Collagen |
|---|---|
| "nitrile" | 25.0 |
| Aspirin | 1.5 |
| Indomethacin | 0.4 |

Table 5

Effect of Incubation of "Nitrile" in Whole Blood on Collagen-Induced Platelet Aggregation

| Drug conc. (µM) | Expt. I Δ light transmission units* | Expt. I percent inhibition | Expt. II Δ light transmission units* | Expt. II percent inhibition | Expt. III Δ light transmission units* | Expt. III percent inhibition |
|---|---|---|---|---|---|---|
| 0 | 20 | — | 21 | — | 30 | — |
| 100 | 4 | 80 | 4 | 81 | 6 | 80 |
| 50 | 8 | 60 | 9 | 57 | 10 | 67 |
| 25 | 9 | 55 | 10 | 52 | 13 | 57 |
| 10 | 13 | 35 | 13 | 38 | 17 | 43 |
| 5 | 14 | 30 | 15 | 29 | 20 | 33 |
| 1 | 18 | 10 | 19 | 9.5 | 27 | 10 |

*mean of duplicate determinations

Table 6

Acute Toxicity and Ulcerogenic Activity

| | (a) Acute toxicity(mice) LD$_{50}$ mg/kg i.p. | (a) Acute toxicity(mice) LD$_{50}$ mg/kg p.o. | (b) Ulcer incidence(rats) ED$_{50}$ mg/kg p.o. |
|---|---|---|---|
| "nitrile" | 750 | >1000 | >250 |
| Aspirin | — | >1000 | 49 |
| Indomethacin | 193 | 430 | 3 |

Table 7

Inhibition of Collagen-Induced Platelet Aggregation

| | Activity IC$_{50}$ (µM) |
|---|---|
| "nitrile" | 3.5 |
| "amide" | 3.0 |

The following examples illustrate typical formulations containing the "nitrile" and the "amide" as the active ingredient(s).

EXAMPLE 47

TABLET FORMULATIONS:- (Wet Granulation)

| Item | Ingredients | mg/tablet | mg/tablet | mg/tablet | mg/tablet |
|---|---|---|---|---|---|
| 1. | 3-Phenyl-5-[2,2,2-trifluoro-1-hydroxy-1-(trifluoromethyl)ethyl]indole-2-carboxamide | 1 | 5 | 10 | 25 |
| 2. | Lactose | 202 | 232 | 261 | 280 |
| 3. | Modified starch | 25 | 35 | 45 | 55 |
| 4. | Pregelatinized starch | 20 | 25 | 30 | 35 |

| | TABLET FORMULATIONS:- (Wet Granulation) | | | | |
|---|---|---|---|---|---|
| Item | Ingredients | mg/tablet | mg/tablet | mg/tablet | mg/tablet |
| 5. | Magnesium stearate | 2 | 3 | 4 | 5 |
| | Weight of tablet | 250 | 300 | 350 | 400 |
| PROCEDURE: | | | | | |
| (1) | Mix Items 1–4 in a suitable mixer. | | | | |
| (2) | Granulate with sufficient distilled water to proper consistency. Mill. | | | | |
| (3) | Dry in a suitable oven. | | | | |
| (4) | Mill and mix with magnesium stearate for 3 minutes. | | | | |
| (5) | Compress on a suitable press equipped with approximate punches. | | | | |

EXAMPLE 48

| | CAPSULE FORMULATIONS: | | | | |
|---|---|---|---|---|---|
| Item | Ingredients | mg/capsule | mg/capsule | mg/capsule | mg/capsule |
| 1. | 3-Phenyl-5-[2,2,2-trifluoro-1-hydroxy-1-(trifluoromethyl)ethyl]indole-2-carboxamide | 1 | 5 | 10 | 25 |
| 2. | Lactose | 203 | 293.5 | 328 | 372.5 |
| 3. | Starch | 30 | 35 | 40 | 30 |
| 4. | Talc | 15 | 15 | 20 | 20 |
| 5. | Dioctyl sodium sulfosuccinate (Aerosol OT)* | 1 | 1.5 | 2.0 | 2.5 |
| | Capsule fill weight | 250 | 350 | 400 | 450 |
| PROCEDURE: | | | | | |
| 1) | Mix Items 1, 2, 3 and 5 in a suitable mixer. Mill. | | | | |
| 2) | Add talc and mix well. | | | | |
| 3) | Encapsulate on suitable equipment. | | | | |

*American Cyanamid

EXAMPLE 49

| | CAPSULE FORMULATIONS: | | | | |
|---|---|---|---|---|---|
| Item | Ingredients | mg/capsule | mg/capsule | mg/capsule | mg/capsule |
| 1. | 3-Phenyl-5-[2,2,2-trifluoro-1-hydroxy-1-(trifluoromethyl)ethyl]indole-2-carbonitrile | 1 | 5 | 10 | 25 |
| 2. | Lactose | 203 | 293.5 | 328 | 372.5 |
| 3. | Starch | 30 | 35 | 40 | 30 |
| 4. | Talc | 15 | 15 | 20 | 20 |
| 5. | Dioctyl sodium sulfosuccinate (Aerosol OT)* | 1 | 1.5 | 2.0 | 2.5 |
| | Capsule fill weight | 250 | 350 | 400 | 450 |
| PROCEDURE: | | | | | |
| (1) | Mix Items 1, 2, 3 and 5 in a suitable mixer. Mill. | | | | |
| (2) | Add talc and mix well. | | | | |
| (3) | Encapsulate on suitable equipment. | | | | |

*American Cyanamid

EXAMPLE 50

| | EXAMPLE 50 TABLET FORMULATIONS: (Direct Compression) | | | | |
|---|---|---|---|---|---|
| Item | Ingredients | mg/tablet | mg/tablet | mg/tablet | mg/tablet |
| 1. | 3-Phenyl-5-[2,2,2-trifluoro-1-hydroxy-1-(trifluoromethyl)ethyl]indole-2-carboxamide | 1 | 5 | 10 | 25 |
| 2. | Lactose | 221 | 217 | 212 | 181 |
| 3. | Microcrystalline cellulose (Avicel)* | 45 | 45 | 45 | 55 |
| 4. | Direct Compression Starch | 30 | 30 | 30 | 35 |
| 5. | Magnesium Stearate | 3 | 3 | 3 | 4 |
| | Weight of tablet | 300 | 300 | 300 | 300 |
| PROCEDURE: | | | | | |
| (1) | Mix Item 1 with equal amount of lactose. Mix well. | | | | |
| (2) | Mix with Items 3, 4, and remaining amount of Item 2. Mix well. | | | | |
| (3) | Add magnesium stearate and mix for 3 minutes. | | | | |
| (4) | Compress on a suitable press equipped with appropriate punches. | | | | |

*FMC Corp., Philadelphia, Pa.

EXAMPLE 51

TABLET FORMULATIONS:- Wet Granulation

| Item | Ingredients | mg/tablet | mg/tablet | mg/tablet | mg/tablet |
|---|---|---|---|---|---|
| 1. | 3-Phenyl-5-[2,2,2-trifluoro-1-hydroxy-1-(trifluoromethyl)ethyl]indole-2-carbonitrile | 1 | 5 | 10 | 20 |
| 2. | Lactose | 202 | 232 | 261 | 280 |
| 3. | Modified starch | 25 | 35 | 45 | 55 |
| 4. | Pregelatinized starch | 20 | 25 | 30 | 35 |
| 5. | Magnesium stearate | 2 | 3 | 4 | 5 |
|  | Weight of tablet | 250 | 300 | 350 | 400 |

PROCEDURE:
(1) Mix Items 1–4 in a suitable mixer.
(2) Granulate with sufficient distilled water to proper consistency. Mill.
(3) Dry in a suitable oven.
(4) Mill and mix with magnesium stearate for 3 minutes.
(5) Compress on a suitable press equipped with appropriate punches.

EXAMPLE 52

EXAMPLE 52 TABLET FORMULATIONS: (Direct Compression)

| Item | Ingredients | mg/tablet | mg/tablet | mg/tablet | mg/tablet |
|---|---|---|---|---|---|
| 1. | 3-Phenyl-5-[2,2,2-trifluoro-1-hydroxy-1-(trifluoromethyl)ethyl]indole-2-carbonitrile | 1 | 5 | 10 | 25 |
| 2. | Lactose | 221 | 217 | 212 | 181 |
| 3. | Avicel | 45 | 45 | 45 | 55 |
| 4. | Direct Compression Starch | 30 | 30 | 30 | 35 |
| 5. | Magnesium Stearate | 3 | 3 | 3 | 4 |
|  | Weight of tablet | 300 | 300 | 300 | 300 |

PROCEDURE:
(1) Mix Item 1 with equal amount of lactose. Mix well.
(2) Mix with Items 3, 4 and remaining amount of Item 2. Mix well.
(3) Add magnesium stearate and mix for 3 minutes.
(4) Compress on a suitable press equipped with appropriate punches.

We claim:
1. A compound of the formula:

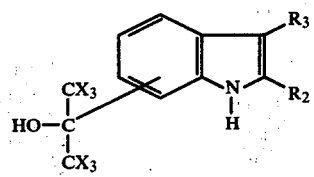

wherein X is chlorine or fluorine; $R_2$ is cyano or carboxamido; and $R_3$ is hydrogen, lower alkyl having 1 to 8 carbon atoms or aryl selected from the group consisting of phenyl and naphthyl wherein said phenyl can be unsubstituted or substituted with a group selected from lower alkyl having 1 to 8 carbon atoms, halogen, amino, lower alkoxy having 1 to 8 carbon atoms, nitro, mono(-lower alkyl having 1 to 8 carbon atoms) amino and di(lower alkyl having 1 to 8 carbon atoms) amino.

2. The compound of claim 1 wherein said compound is

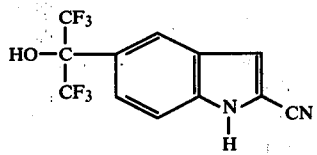

3. The compound of claim 1 wherein said compound is

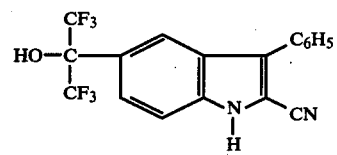

4. The compound of claim 1 wherein said compound is

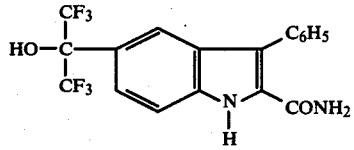

5. A compound of the formula:

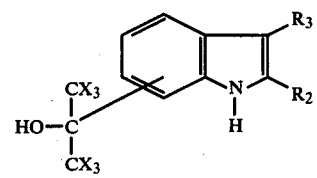

wherein X is chlorine or fluorine; $R_2$ is carboxy, halocarbonyl or lower alkoxycarbonyl with the alkoxy moiety thereof having 1 to 8 carbon atoms; and $R_3$ is hydrogen, lower alkyl having 1 to 8 carbon atoms or aryl selected from the group consisting of phenyl and naphthyl wherein said phenyl can be unsubstituted or substituted with a group selected from lower alkyl having 1 to 8 carbon atoms, halogen, amino, lower alkoxy having 1 to 8 carbon atoms, nitro, mono(lower alkyl having 1 to 8 carbon atoms) amino and di(lower alkyl having 1 to 8 carbon atoms) amino.

6. The compound of claim 1 or 5 wherein $R_3$ is phenyl.

* * * * *